(12) United States Patent
Guggenheim et al.

(10) Patent No.: US 10,286,097 B2
(45) Date of Patent: May 14, 2019

(54) DEODORIZING DEVICE FOR A VEHICLE

(75) Inventors: Rudolf Guggenheim, Zollikon (CH); Beat Keller, Zurich (CH)

(73) Assignee: Supair-Tel AG, Glattbrugg (CH)

( * ) Notice: Subject to any disclaimer, the term of this patent is extended or adjusted under 35 U.S.C. 154(b) by 830 days.

(21) Appl. No.: 14/007,467

(22) PCT Filed: Nov. 30, 2011

(86) PCT No.: PCT/CH2011/000290
§ 371 (c)(1),
(2), (4) Date: Nov. 4, 2013

(87) PCT Pub. No.: WO2012/129709
PCT Pub. Date: Oct. 4, 2012

(65) Prior Publication Data
US 2014/0051344 A1    Feb. 20, 2014

(30) Foreign Application Priority Data
Mar. 29, 2011   (DE) .................. 10 2011 001 637

(51) Int. Cl.
*B60H 3/00*   (2006.01)
*A61L 9/12*   (2006.01)

(52) U.S. Cl.
CPC .............. *A61L 9/12* (2013.01); *B60H 3/0028* (2013.01); *A61L 2209/133* (2013.01); *A61L 2209/15* (2013.01); *B60H 3/0007* (2013.01)

(58) Field of Classification Search
CPC .. A61L 2209/133; A61L 2209/15; A61L 9/12; B60H 3/0028; B60H 3/0007
(Continued)

(56) References Cited

U.S. PATENT DOCUMENTS 3,466,966 A * 9/1969 Brown ................. F16B 21/084
                                                         411/510
3,483,787 A * 12/1969 Saunders ............. F16B 19/004
                                                         411/510
(Continued)

FOREIGN PATENT DOCUMENTS

DE     102009006192 A1   7/2010
EP         1902736 A1    3/2008
(Continued)

OTHER PUBLICATIONS

Search Report for Chinese Application 201180067412.1 dated Feb. 2, 2015.
(Continued)

*Primary Examiner* — Gregory L Huson
*Assistant Examiner* — Frances F. Hamilton
(74) *Attorney, Agent, or Firm* — McCormick, Paulding & Huber LLP (57) ABSTRACT

The invention relates to a deodorization device (1) for a vehicle, with a container (2) for a deodorant (3), wherein the container (2) for the deodorant (3) is provided with at least one opening (7, 8), and with a holding device (4) for mounting the deodorization device (1) on a ventilation slot in the interior of a vehicle, wherein the holding device (4) comprises at least one clamping part (6). The at least one clamping part (6) is made of elastic material, has an elliptical or circular cross section and is configured so as to be able to be introduced in a holding manner into a ventilation slot of a vehicle.

10 Claims, 7 Drawing Sheets

(58) Field of Classification Search
USPC .......................................................... 454/157
See application file for complete search history.

(56) References Cited

U.S. PATENT DOCUMENTS

| | | | | |
|---|---|---|---|---|
| 4,420,859 | A * | 12/1983 | Hammerle | F16B 21/06 24/595.1 |
| 4,486,133 | A * | 12/1984 | Pletcher | F16B 37/046 411/337 |
| 4,571,136 | A * | 2/1986 | Peek | B60N 3/046 24/104 |
| 4,764,068 | A * | 8/1988 | Crispell | F16B 35/005 411/393 |
| 4,776,739 | A | 10/1988 | Hamman | |
| 5,018,921 | A * | 5/1991 | Pinney | F16B 7/0446 403/297 |
| 5,232,322 | A * | 8/1993 | Regensburger | F16B 21/084 411/33 |
| 5,387,065 | A * | 2/1995 | Sullivan | F16B 19/1081 411/45 |
| 5,762,549 | A | 6/1998 | Scheuer et al. | |
| 6,080,059 | A * | 6/2000 | Kim | B60H 3/06 454/155 |
| 6,102,660 | A * | 8/2000 | Lee | B60H 3/0028 416/146 R |
| 6,129,175 | A * | 10/2000 | Tutor | A61F 11/08 128/864 |
| 6,342,003 | B1 * | 1/2002 | Wang | B60H 1/345 422/122 |
| 6,416,043 | B1 * | 7/2002 | Eisenbraun | A61L 9/12 261/104 |
| 7,025,283 | B2 * | 4/2006 | Torres | A61L 9/127 239/34 |
| 7,503,528 | B2 * | 3/2009 | Adams | F16B 5/0685 24/297 |
| 7,687,037 | B2 * | 3/2010 | Wheatley | A61L 9/03 422/123 |
| 7,780,094 | B2 * | 8/2010 | Caserta | A61L 9/127 239/289 |
| 7,790,000 | B2 * | 9/2010 | Matsuda | A01M 1/2044 159/27.3 |
| 7,862,272 | B2 * | 1/2011 | Nakajima | F16B 21/084 411/41 |
| 8,672,601 | B2 * | 3/2014 | Nitsche | F16B 19/004 24/292 |
| D709,609 | S * | 7/2014 | Hatfield | A61F 11/08 D24/106 |
| 9,021,765 | B2 * | 5/2015 | Ziehm | B60R 13/0206 24/297 |
| 9,458,876 | B2 * | 10/2016 | Morris | F16B 39/284 |
| 2003/0235522 | A1 * | 12/2003 | Harrop | A61L 9/12 422/120 |
| 2004/0003724 | A1 * | 1/2004 | Ellis | A01M 1/205 96/115 |
| 2004/0050950 | A1 * | 3/2004 | Brown | A61L 9/12 239/55 |
| 2005/0127538 | A1 | 6/2005 | Fabrega et al. | |
| 2005/0169793 | A1 * | 8/2005 | Wheatley | A61L 9/048 422/5 |
| 2007/0001025 | A1 * | 1/2007 | Caserta | A61L 9/127 239/59 |
| 2007/0057084 | A1 * | 3/2007 | Vieira | A61L 9/12 239/34 |
| 2009/0114736 | A1 * | 5/2009 | Janakat | A61L 9/127 239/44 |
| 2010/0019059 | A1 * | 1/2010 | Bulsink | A61L 9/127 239/55 |
| 2010/0196091 | A1 * | 8/2010 | Selle | F16B 5/0628 403/409.1 |
| 2010/0314461 | A1 * | 12/2010 | Gruenbacher | A61L 9/12 239/6 |
| 2012/0225408 | A1 * | 9/2012 | Moore | A61C 8/0033 433/174 |

FOREIGN PATENT DOCUMENTS

| | | | | |
|---|---|---|---|---|
| FR | 2756184 B1 * | 7/2000 | | A61L 9/122 |
| IT | MI20091982 A1 | 5/2011 | | |
| JP | S63-6207 | 1/1988 | | |
| JP | 2000185588 A | 7/2000 | | |
| JP | 2001-503043 A | 3/2001 | | |
| JP | 2005308054 A * | 11/2005 | | |
| JP | 2008-114078 A | 5/2008 | | |
| WO | WO 02066272 A2 * | 8/2002 | | B60H 1/34 |
| WO | 2011058093 A1 | 5/2011 | | |

OTHER PUBLICATIONS

International Search Report for PCT/CH2011/000290 dated Apr. 12, 2012.

* cited by examiner

DEODORIZING DEVICE FOR A VEHICLE

REFERENCE TO RELATED APPLICATIONS

This application claims priority on German Patent Application No. 10 2011 001637.6 which was filed on Mar. 29, 2011 and International Patent Application No. PCT/CH2011/000290 filed Nov. 30, 2011, the entire disclosures of which are hereby incorporated by reference.

TECHNICAL FIELD

The invention relates to a deodorizing device for a vehicle and comprises a container with an opening, a deodorant within the container, and a holding device for holding the deodorant device in a ventilation slot in the vehicle. The term "vehicle" here refers to both land vehicles such as passenger cars and trucks as well as aircraft.

PRIOR ART

A deodorizing device for the interior of a vehicle is known from the patent application DE 10 2009 006 192 A1. The deodorizing device comprises a flask for deodorant accommodated within an enclosure having an air inlet opening and an air outlet opening. The deodorizing device can be disposed in the interior of a vehicle by means of a pipe at the rear center nozzle. The pipe is connected to the air inlet opening so that a stream of air conveyed by a diaphragm pump flows with preconditioned and purified air from the interior of the vehicle through the pipe and the air inlet opening into the interior of the enclosure and onward around the bottle to the upper area of the enclosure where it passes through openings into the interior of the flask and contacts the surface of the deodorant. The stream of air now enriched with deodorant molecules flows to the interior of the vehicle through an outlet pipe and the air outlet opening in the enclosure.

SUMMARY OF THE INVENTION

The function of the invention is to provide a deodorization device for a vehicle which is simply constructed and is user friendly in that it is able to be simply and securely mounted to the interior of a vehicle, and which enables the efficient deodorizing of the interior of a vehicle.

The invented deodorization device comprises a container for a deodorant with a holding device for mounting the deodorization device on a ventilation slot in the interior of a vehicle, in particular to a ventilation slot of a rear center nozzle of a vehicle. The container for a deodorant has one or more openings. The holding device comprises at least one clamping part made from elastic material having an elliptical or circular cross-section. The clamping part is configured so as to be able to be introduced in a holding manner into a ventilation slot of a vehicle.

The transverse direction of the clamping part is defined as that direction running perpendicular to the direction in which the clamping part extends. The direction in which the clamping part extends corresponds to its longitudinal direction. An ellipse is defined herein as an oval closed curve (http://de.wikipedia.org/wiki/Ellipse) [EN: http://en.wikipedia.org/wiki/Ellipse].

The at least one clamping part of the invented deodorization device in the preferred embodiment has an outer shape in the form of an elliptical paraboloid, equivalent to a cone or cylinder, wherein the extreme value of the paraboloid or apex of the cone faces away from the container for the deodorant. The outer shape is understood as the three-dimensional variant of an envelope (http://de.wikipedia.org/wiki/Einhüllende) [EN: http://en.wikipedia.org/wiki/Envelope_(mathematics). The extreme value is to be understood as the paraboloid maximum point in the longitudinal direction of the clamping part.

The clamping part is preferably made from or comprises silicon, rubber and/or a thermoplastic elastomer as preferred material, whereby the material of the clamping part preferably has a hardness in the range of Shore 30A to Shore 90A.

The deodorization device to which the invention relates is able to be introduced into a ventilation slot in the interior of a vehicle simply by means of the at least one clamping part and is kept stable and secure by said clamping part even during movement or shaking of the vehicle. By mounting the deodorization device to a ventilation slot in the interior of a vehicle, air exiting through the ventilation slot is able to come into contact with the deodorant through one or more openings provided in the container for the deodorant, thereby being enriched with the molecules of the deodorant in such a way that the air enriched with the deodorant molecules enters the interior of the vehicle and efficiently deodorizes it.

BRIEF DESCRIPTION OF THE DRAWINGS

Further advantageous embodiments of the invention are set forth in the dependent claims and the following examples of carrying out the invention illustrated by the drawings. Illustrated are:

In the figures, the like reference numerals indicate the same component or a component with the same function. Dimension and size information in the figures are only exemplary in character and given in millimeters as the unit.

DESCRIPTION OF THE PREFERRED EMBODIMENTS

FIGS. 1 through 7 show a deodorization device in accordance with the invention 1 having a container 2 for a deodorant 3 and having a holding device 4 for mounting the deodorizing device 1 to a ventilation slot in the interior of a vehicle. The deodorant 3 is preferably in the form of a replaceable scented stick 5. The rear view illustrated in FIG. 5 of the deodorization device 1 corresponds to the ventilation slot side of the deodorization device 1 when the deodorization device 1 is mounted to the ventilation slot. The front view illustrated in FIG. 4 of the deodorization device 1 corresponds to the side opposite the rear view of the deodorization device 1. The holding device 4 is disposed at the side of the deodorization device 1 facing the ventilation slot when the deodorization device 1 is mounted.

The holding device 4 comprises at least one clamping part 6 made from elastic material having an elliptical or circular cross-section. The clamping part 6 is configured so as to be able to be introduced in a holding manner into a ventilation slot of a vehicle. That is, the dimensions of the elliptical or circular cross-section of the clamping part 6 are selected depending on the dimensions, in particular the width, of the ventilation slot in such a way that the deodorization device 1 is able to be mounted to the ventilation slot when the at least one clamping part 6 is inserted/introduced into the ventilation slot and is retained there by said clamping part 6 in a holding manner.

The container 2 has one, preferably multiple, openings 7 provided on the same side as the holding device 4. When the deodorization device 1 is mounted, air flows out of the ventilation slot through these openings 7 into the container 2, comes in contact with the deodorant 3, and is enriched with the molecules of the deodorant. The container 2 has one, preferably multiple, openings 8 situated opposite one, preferably multiple, openings 7 through which the enriched air exits into the interior of the vehicle and is able to deodorize said interior. The openings 8 point to the interior of vehicle when the deodorization device is mounted. In addition or as an alternative to the openings 8, openings can also be provided to one or both side walls of the container 2 and/or its bottom side.

The container 2 is affected preferably in an elongated manner and provided with at least two clamping parts 6 (as illustrated in FIGS. 1 through 7) wherein each clamping part 6 is arranged at a lateral end area of the container 2. When it is mounted to ventilation slot, the container 2 extends along the ventilation slot wherein the two clamping parts 6 are arranged at the same ventilation slot. It is also certainly possible to arrange the container 2 transverse to the ventilation slot wherein the clamping parts 6 are introduced into different ventilation slots.

The container for the deodorant can also be effected, for example, in a circular shape wherein the holding device having the one or more clamping parts is provided, preferably centered, on the rear side, that is, the side facing the ventilation slot when mounted, of the container. This embodiment is especially suited to circular-shaped ventilation slots as frequently found in the case of a circular-shaped rear center nozzle.

The container 2 preferable comprises a removable cover 10 and removable side walls 11. Furthermore, an the container 2 is preferable provided with an adjustable slider 12 with which the openings 7,8 may be at least partially closed and the deodorizing may be regulated by this means. The slider 12 is preferably disposed within the container 2 and has one tab 13 for each opening 7,8, the tab 13 extending parallel to the opening assigned to it and having the ability to be moved in front of this opening. The slider 12 partially encloses the deodorant 3 or the scented stick 5 with the tabs 13. The slider 12 preferably has a grip 14 by means of which it can be moved manually in the longitudinal direction of the container 2 in order to close the openings 7,8. The cover 10 of the container 2 has an opening 15 through which the grip 14 protrudes, such that the user has access to the grip 14 and can move the slider by this means.

The deodorant, as illustrated in FIGS. 1 through 7, is preferably provided in the form of a scented stick 5, whereby the scented stick 5 comprises as material a composite made from at least one polymer, in particular an elastomer, and the deodorant, or is made from such material. The polymer is enriched with the deodorant and functions as its carrier. The scented stick 5 preferably has multiple outlet openings 16 through which the exiting air is able to flow from the ventilation slot. Provision of the outlet openings 16 enlarges the surface area on which air flowing from the ventilation slot comes into contact with the deodorant, resulting in increased enrichment with deodorant molecules of the air flowing through the deodorization device 1. The outlet openings 16 are preferably aligned with the direction of the air current from the ventilation slot. A scented stick of this type is already known from the Italian Patent Application No. MI2009 A001982 and International Patent Application No. PCT/EP2010/067277, to which reference is hereby made.

Alternatively, the deodorant is also capable of being provided in the form of a granulate, the granulate being contained in a cage disposed in the container 2.

Figure 1:
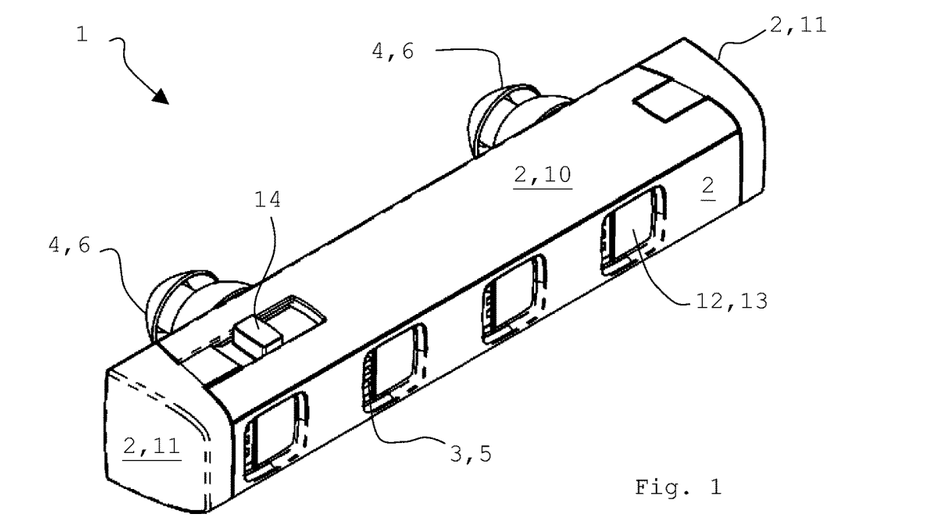
FIG. 1 a perspective view of a deodorization device in accordance with the invention, FIG. 2 a top view of a deodorization device in accordance with the invention, FIG. 3 a cross-section of a deodorization device in accordance with the invention along the cut line A-A' in FIG. 2, FIG. 4 a front view of a deodorization device in accordance with the invention, FIG. 5 a rear view of a deodorization device in accordance with the invention, FIG. 6 a side view of a deodorization device in accordance with the invention, FIG. 7 an exploded view of a deodorization device in accordance with the invention.
Figure 2:
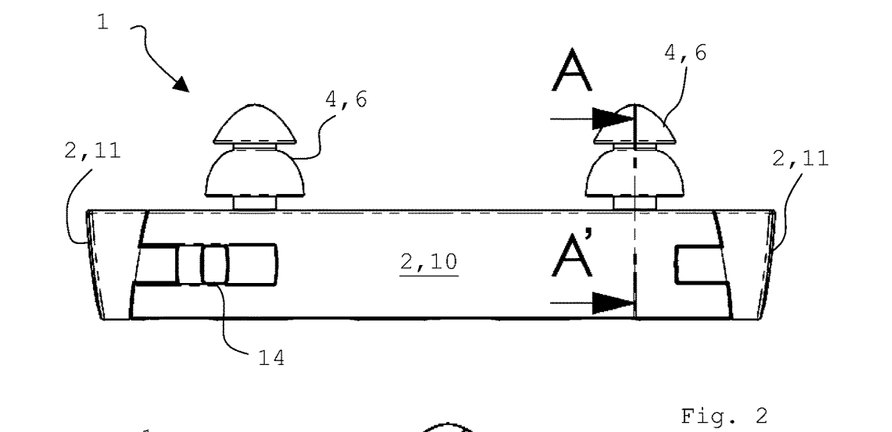
Figure 3:
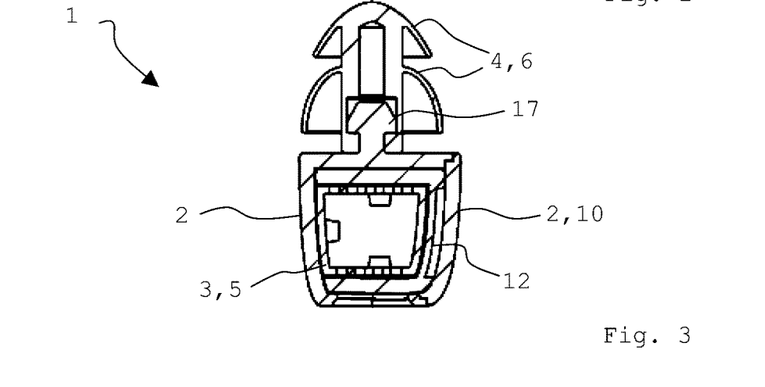
Figure 4:
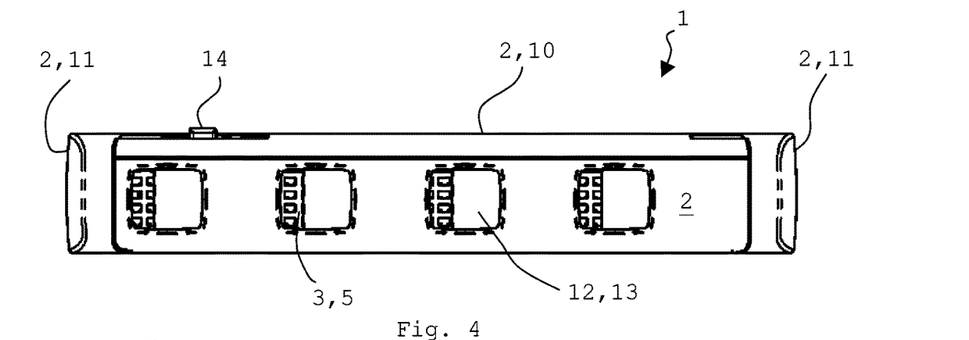
Figure 5:
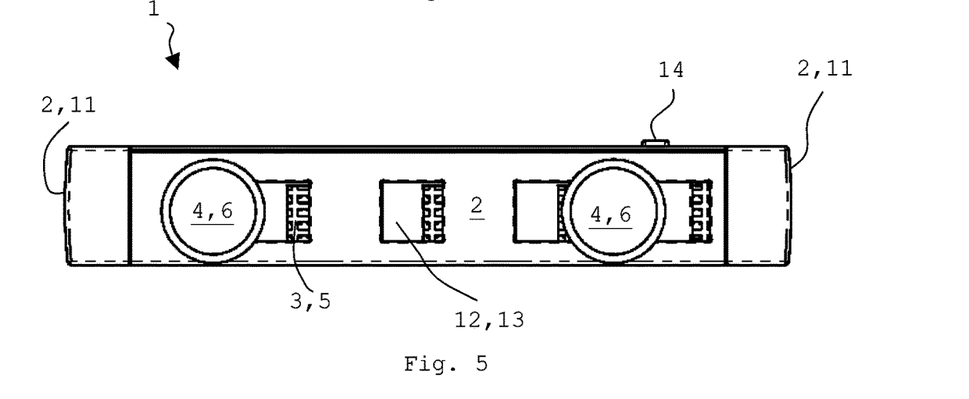
Figure 6:
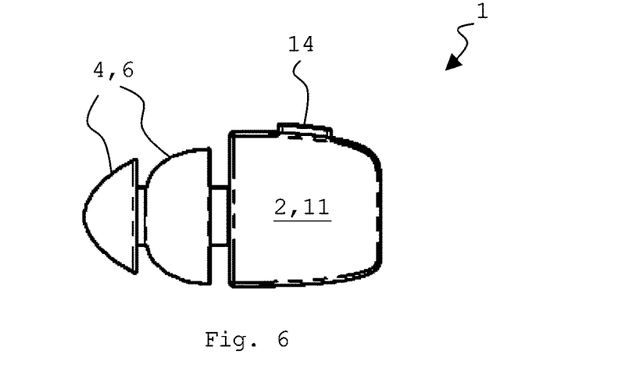
Figure 7:
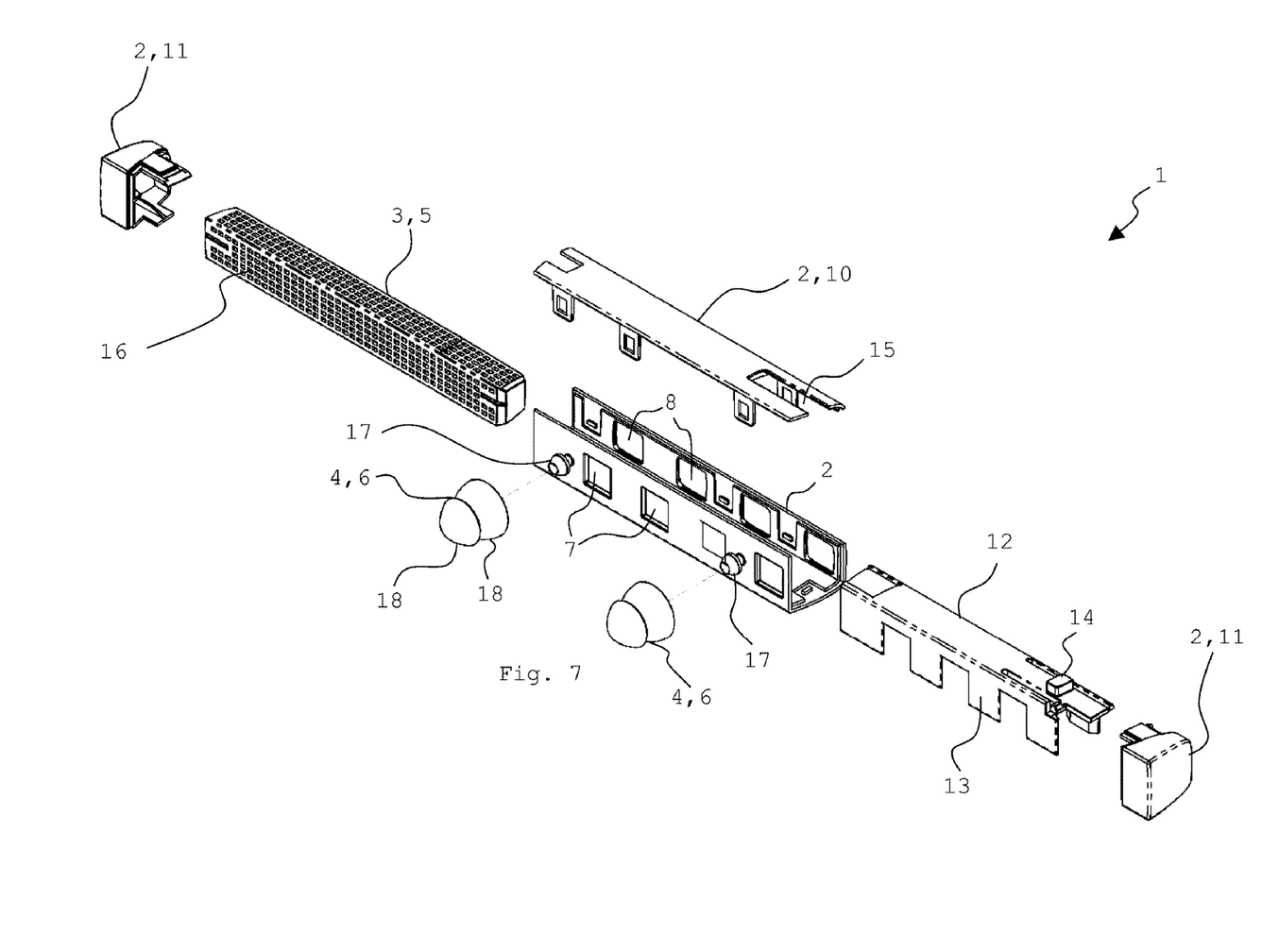
Figure 8:
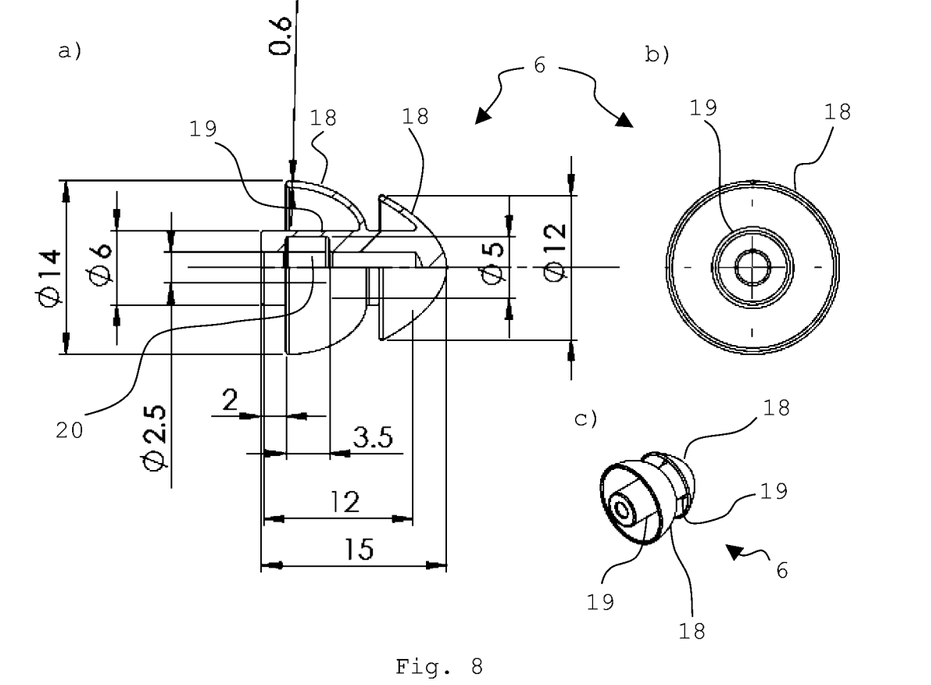
FIGS. 8a, 8b, and 8c are views of a clamping part of a deodorization device in accordance with the invention as a longitudinal section (FIG. 8a)), as a bottom view (FIG. 8b)) and in perspective (FIG. 8c))

As illustrated for example in FIGS. 6 and 8, the clamping part 6 comprises preferably two panels 18 which have the form of an elliptical paraboloid, wherein the extreme value, that is, the maximum point of each elliptical paraboloid, faces away from the container 2. The expression "the form of an elliptical paraboloid" also hereby includes the form of a frustum of an elliptical paraboloid. Alternatively, the one or more panels can have the external shape of a truncated cone. The one or more panels of the clamping part can also have the form of a paraboloid of revolution or of a truncated cone with a circular base. Alternatively, the one or more panels can have the form of an elliptical paraboloid with an oval base or of a truncated cone with an oval base. The panels are arranged one after the other in the longitudinal direction of the clamping part 6. Of course, the clamping part 6 can also have only one screen or more than two screens. In these cases, the one or more panels 18 of the clamping part 6 fit within the outer shape of the clamping part 6 defined at the outset or within its envelope.

Preferably, the closer to the container 2 a panel 18 is disposed when the clamping part 6 is attached to the container, the larger its area in comparison to other panels of clamping part 6 if provided, thereby enabling introduction of the clamping part 6 into the ventilation slot. FIG. 8 shows exemplary dimensions of a clamping part 6 with two panels 18, each panel having the form of an elliptical paraboloid. The clamping part 6 has a shaft 19 through which the panels 18 are connected to one another at their center.

The one or more clamping parts 6 are preferably manufactured by injection molding. Thus the clamping parts 6 can be directly attached to the container 2. Alternatively, each clamping part 6 can be affixed to the container 2 by means of a screw coupling or a snap fastening. A snap fastening, for example, can be effected by means of one retaining cam 17 for each clamping part 6 on the side of the container 2 facing the clamping part onto which the respective clamping part is attached (see FIGS. 3 and 7). The clamping part 6 has a recess 20 on the side facing the container 2 into which the retaining cam 17 snaps when applying/attaching the clamping part (see FIG. 8).

Furthermore, for the purpose of affixing each clamping part 6, the container 2 can have a pin pointing out from it onto which each clamping part 6 is attached. For this, the clamping part 6 has an elongated recess into which the pin is introduced, the diameter of the pin preferably being somewhat larger than the diameter of the elongated recess for firm holding. The pin can have lateral projections and the elongated recess can have lateral depressions, wherein the lateral projections of the pin are introduced into the lateral depressions of the elongated recess for the purpose of attaching a clamping part 6 to the container 2, thereby obtaining a snap fastening. Alternatively, the pin can have lateral depressions and the elongated recess can have inward-pointing projections on its interior, wherein, for the purpose of attaching a clamping part 6 to the container 2, the inward pointing projections of the elongated recess are introduced into the lateral depressions of the pin, likewise resulting in a snap fastening. Alternatively or additionally, the pin and the elongated recess can be connected to each other by means of an adhesive.

Alternatively, each clamping part 6 can have an elastic fastening member on the side facing the container 2, which can be effected by means of a passage through the side of the container 2 facing the holding device 4 and which engages behind the wall of the container 2 facing the holding device 4. A snap fastening is also thereby obtained.

Figure 9:
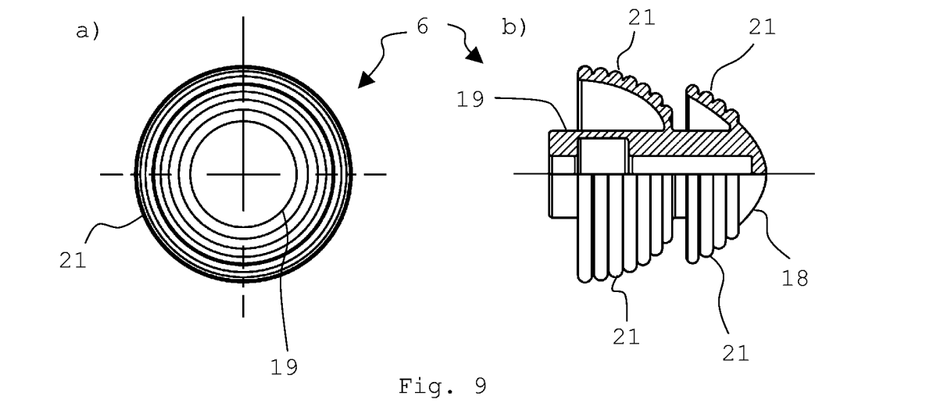
FIGS. 9a and 9b are views of a clamping part of a deodorization device in accordance with the invention wherein said clamping part is provided with protrusions as a bottom view (FIG. 9a)), as a longitudinal section (FIG. 9b) upper half) and as a side view (FIG. 9b), lower half)

On the exterior side of the one or more panels 18, as shown in FIG. 9, protrusions 21 pointing outward are provided wherein each protrusion 21 extends in a cross-sectional plane along the periphery of the associated panel 18 and closes around the respective panel 18, thus forming a circular or oval shape. This enables better gripping of the clamping part 6 and therefore of the invented deodorization device 1 to a ventilation slot in the interior of a vehicle. The protrusions can be rounded (as represented in FIG. 9*b*)) end with a peak or be tapered, or be embodied as ribs, wherein ribs are understood to be a thin disc or plate.

Figure 12:
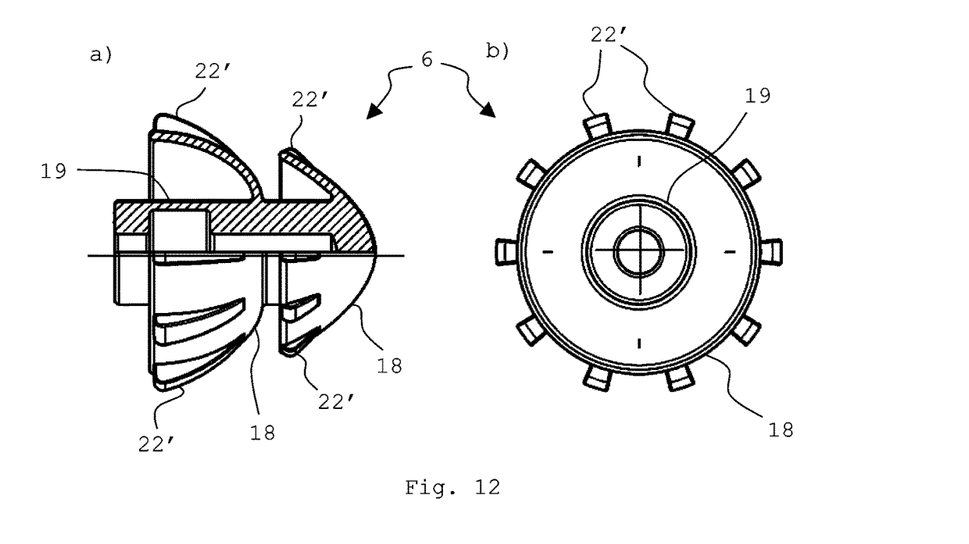
FIGS. 12a and 12b are views of a clamping part of a deodorization device in accordance with the invention wherein said clamping part is provided with support members as a longitudinal section (FIG. 12a) upper half), as a side view (FIG. 12a), lower half) and as a bottom view (FIG. 12b)), lower half) in a third embodiment.
Figure 13:
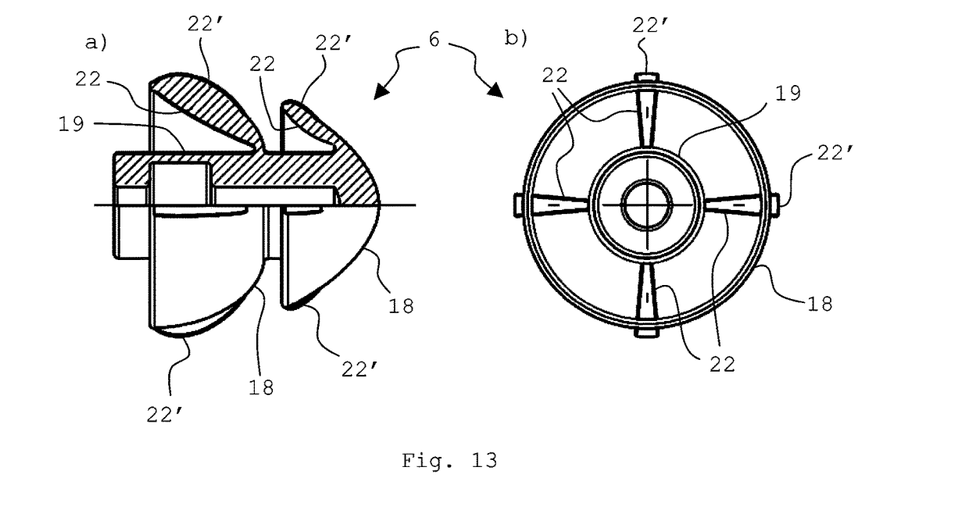
FIGS. 13a and 13b are views of a clamping part of a deodorization device in accordance with the invention wherein said clamping part is provided with support members as a longitudinal section (FIG. 13a) upper half) as a side view (FIG. 13a), lower half) and as a bottom view (FIG. 13b)), lower half) in a fourth embodiment.

Support members 22, 22' are preferably assigned to the one or more panels 18 of each clamping part 6 for the purpose of supporting the one or more panels 18 (FIGS. 10 through 13), which can be embodied as lamellae or ribs and which extend in the longitudinal direction of the clamping part 6. The support members can be arranged on the interior side of a panel 18 (reference numeral 22 in FIGS. 10 and 11), on its exterior side (reference numeral 22' in FIG. 12) or on its interior and exterior side (reference numeral 22 and 22' in FIG. 13). If the support members 22, 22' are arranged on the interior and exterior side of a panel 18, as shown in FIG. 13, they are preferably disposed across from each other. The support members 22, 22' extend at least partially along the elongated dimension of the panel 18 with which they are associated.

Figure 10:
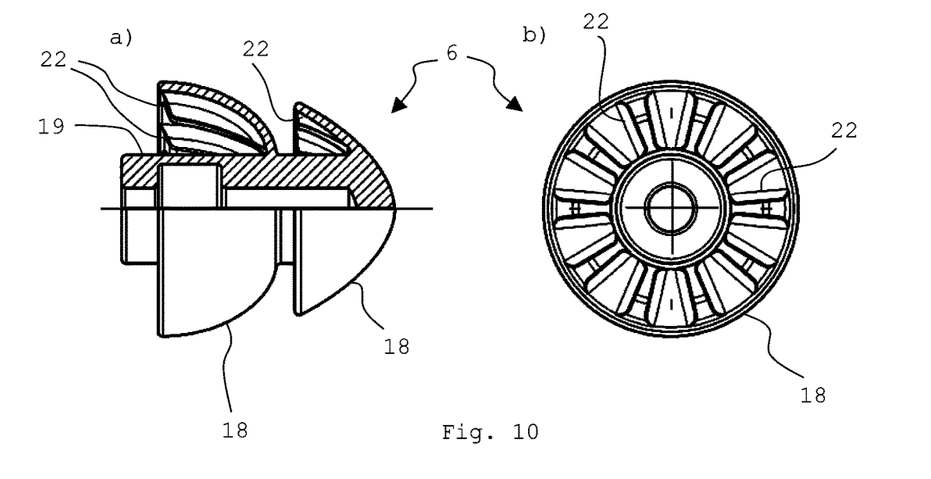
FIGS. 10a and 10b are views of a clamping part of a deodorization device in accordance with the invention wherein said clamping part is provided with support members as a longitudinal section (FIG. 10a) upper half), as a side view (FIG. 10a), lower half) and as a bottom view (FIG. 10b)), lower half) in an initial embodiment.
Figure 11:
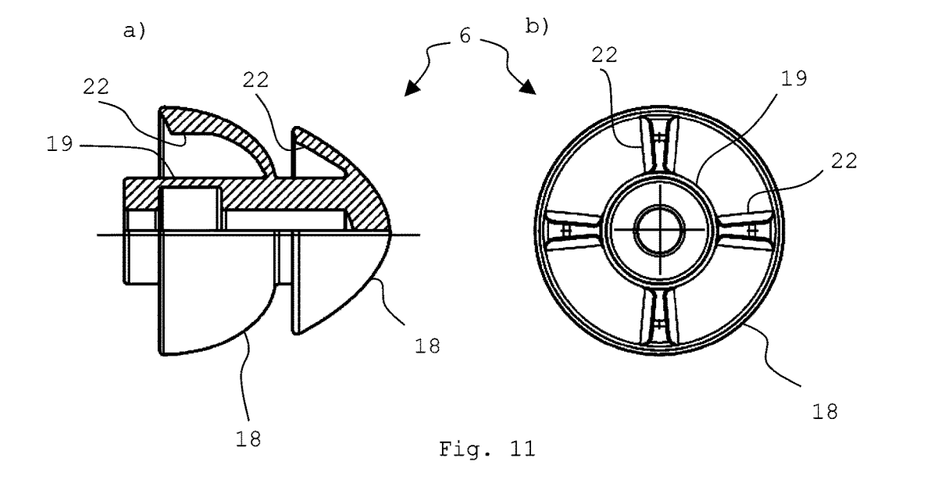
FIGS. 11a and 11b are views of a clamping part of a deodorization device in accordance with the invention wherein said clamping part is provided with support members as a longitudinal section (FIG. 11a) upper half), as a side view (FIG. 11a), lower half) and as a bottom view (FIG. 11b)), lower half) in a second embodiment.

There are preferably at least four support members 22, 22' provided on at least one side of a panel, arranged in a cross-section plane at a 90 degree angle to each other (see FIGS. 11 and 13). However, more support members 22, 22' can be provided on one side of a panel 18, as shown in FIGS. 10 and 12, the angle between two neighboring support members 22, 22' preferably having the same size.

Figure 14:
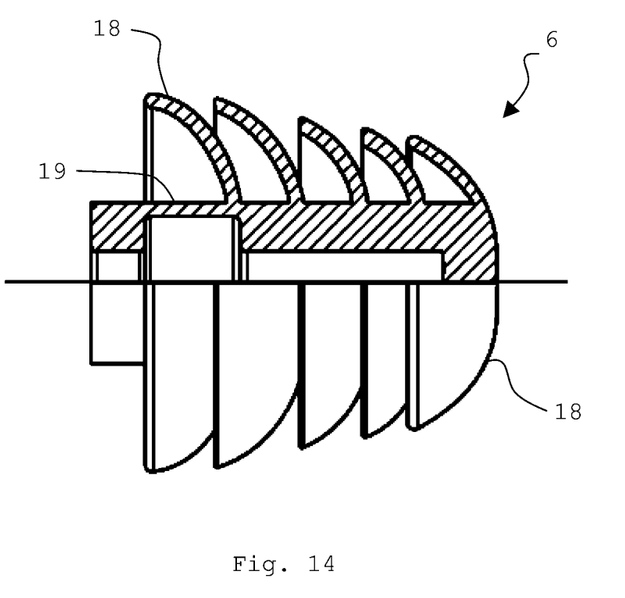
FIG. 14 a longitudinal section (upper half) and a side view (lower half) of a clamping part of a deodorization device in accordance with the invention wherein said clamping part is provided with overlapping panels and FIG. 15 a longitudinal section (upper half) and a side view (lower half) of a clamping part of a device in accordance with the invention wherein said clamping part is provided with ribs.

FIG. 14 illustrates clamping part 6 having an exemplary five panels 18 arranged in succession in a longitudinal direction and having the form of an elliptical paraboloid. The panels 18 are disposed in such a way that they overlap one another in a longitudinal direction of the clamping part 6 at least partially, resulting in increased stability of the clamping part 6.

Figure 15:
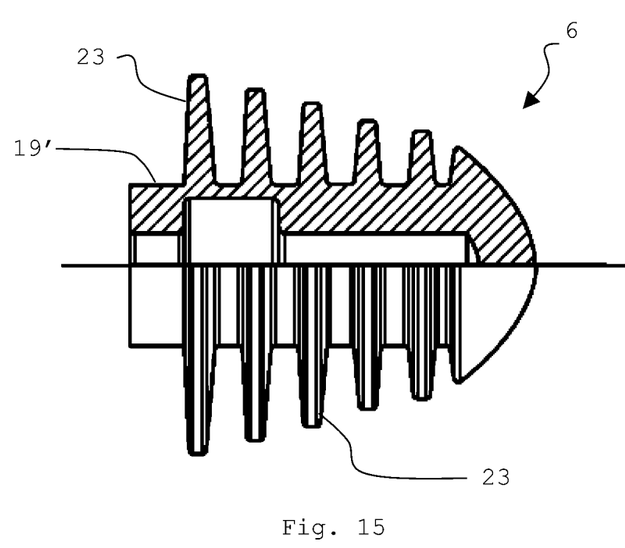

According to an alternative embodiment illustrated in FIG. 15, each clamping part 6 of the invented deodorization device 1 has one or more ribs 23 extending radially in a transverse direction of the clamping part 6. If multiple ribs 23 are provided, these are arranged one after the other in the longitudinal direction of the clamping part 6. The ribs 23 are joined to one another through a shaft 19' extending in the longitudinal direction of the clamping part 6. It is also possible that only one rib 23, disposed so as to run in a spiral formation on the shaft 19', is provided. The dimensions of the one or more ribs 23 are such that they fit within the outer shape of the clamping part 6 defined at the outset or within its envelope.

The at least one clamping part 6 is preferably embodied as a separate part of the deodorization device 1 which can be connected to the deodorization device 1—preferably in a detachable manner. Thus, multiple clamping parts of varying dimensions, in particular varying cross-sections, can be made available to the user having a deodorization device, wherein the multiple clamping parts (for example, three clamping parts) are designed for three different widths of ventilation slots. The user then has the functional advantage of being able to use the same deodorization device in his passenger vehicle, van or truck, which normally have ventilation slots of different widths, by exchanging the one or more clamping parts.

While the preferred embodiments and configuration in the present application describe the invention, it is specifically pointed out that the invention is not limited to these and can be embodied and can be embodied in other ways within the scope of the claims specified below.

The invention claimed is:

1. A deodorization device for a vehicle, the deodorization device having a container for a deodorant, wherein the container is provided with at least one opening for the deodorant, and a holding device for the purpose of mounting the deodorization device onto a ventilation slot in the interior of a vehicle, wherein the holding device comprises at least one exchangeable clamping part, wherein the at least one exchangeable clamping part is made from an elastic material, has a circular or elliptical cross-section, a central shaft, and is configured so as to be able to be introduced in a holding manner into a ventilation slot of a vehicle, wherein the at least one exchangeable clamping part comprises more than one umbrella-like panel, each of the umbrella-like panels being a continuous body of revolution fully encircling the central shaft and having the form of an elliptical paraboloid or a truncated cone, that has a continuous outer periphery and is flexible at the continuous outer periphery, the panels are stacked one after the other in the longitudinal direction of the central shaft, and are provided with support members for the purpose of supporting the panels, the support members being embodied as lamellae and/or ribs, wherein the at least one exchangeable clamping part and the container have a separable connection enabling the exchangeable clamping part to be separable from and connectable to the container.

2. The deodorization device according to claim 1, wherein the at least one exchangeable clamping part has an outer shape in the form of an elliptical paraboloid, equivalent to a cone or cylinder, wherein the extreme value of the paraboloid or apex of the cone or cylinder faces away from the container for the deodorant.

3. The deodorization device according to claim 1 wherein the container has a slider to at least partially close the at least one opening in the container.

4. The deodorization device according to claim 1 wherein the panels of the clamping part have the form of a paraboloid of revolution or the external shape of a truncated cone with a circular base.

5. The deodorization device according to claim 1 wherein protrusions are provided on the exterior side of the panels of the at least one exchangeable clamping part.

6. The deodorization device according to claim 5 wherein the protrusions are of a rounded shape ending with a peak and/or are embodied as ribs.

7. The deodorization device according to claim 1 wherein the at least one exchangeable clamping part comprises silicon, rubber and/or a thermoplastic elastomer as material.

8. The deodorization device according to claim 1 wherein the at least one exchangeable clamping part has a hardness in the range of Shore 30A to Shore 90A.

9. The deodorization device according to claim 1 wherein the container is effected in an elongated manner and provided with at least two exchangeable clamping parts, wherein each exchangeable clamping part is provided at a lateral end area of the elongated container for insertion along a length of the ventilation slot.

10. The deodorization device according to claim 1 wherein the deodorant is provided in the form of a scented stick, wherein the scented stick comprises as material a composite made from at least one polymer and the deodorant, and said scented stick has multiple outlet openings.

* * * * *